(12) United States Patent
Mitchell, Sr. et al.

(10) Patent No.: US 9,637,389 B2
(45) Date of Patent: May 2, 2017

(54) ACTIVATED CARBON MONOLITH CATALYST, METHODS FOR MAKING SAME, AND USES THEREOF

(75) Inventors: Robert L. Mitchell, Sr., Atlanta, GA (US); Lee M. Mitchell, Atlanta, GA (US); Joseph H. Keller, West Chester, PA (US); Jack H. L'Amoreaux, Loganville, GA (US)

(73) Assignee: Applied Technology Limited Partnership, Doraville, GA (US)

( * ) Notice: Subject to any disclaimer, the term of this patent is extended or adjusted under 35 U.S.C. 154(b) by 0 days.

(21) Appl. No.: 12/507,940

(22) Filed: Jul. 23, 2009

(65) Prior Publication Data

US 2009/0326270 A1     Dec. 31, 2009

Related U.S. Application Data

(62) Division of application No. 11/102,452, filed on Apr. 8, 2005, now abandoned.

(51) Int. Cl.
| | | |
|---|---|---|
| *C07B 43/04* | (2006.01) | |
| *C01B 31/08* | (2006.01) | |
| *C07C 209/36* | (2006.01) | |
| *B01J 21/18* | (2006.01) | |
| *B01J 35/04* | (2006.01) | |

(52) U.S. Cl.
CPC ............ *C01B 31/089* (2013.01); *B01J 21/18* (2013.01); *B01J 35/04* (2013.01); *C07B 43/04* (2013.01); *C07C 209/36* (2013.01)

(58) Field of Classification Search
CPC .............................. C07B 43/04; C07C 209/36
See application file for complete search history.

(56) References Cited

U.S. PATENT DOCUMENTS

| | | | | |
|---|---|---|---|---|
| 5,066,628 A * | 11/1991 | Miller et al. | ..................... | 502/66 |
| 5,104,540 A * | 4/1992 | Day | ................... | B01D 39/2027 |
| | | | | 164/134 |
| 5,716,899 A * | 2/1998 | Guile et al. | ................... | 502/439 |
| 5,914,294 A * | 6/1999 | Park et al. | ..................... | 502/417 |
| 5,997,829 A * | 12/1999 | Sekine et al. | ................. | 423/210 |
| 6,097,011 A * | 8/2000 | Gadkaree et al. | ............ | 219/553 |
| 6,136,749 A * | 10/2000 | Gadkaree et al. | ............. | 502/183 |
| 6,455,023 B1* | 9/2002 | Gadkaree | ................. | B01J 21/18 |
| | | | | 208/213 |
| 7,691,773 B2* | 4/2010 | Suh et al. | ..................... | 502/159 |

* cited by examiner

*Primary Examiner* — Stuart Hendrickson
(74) *Attorney, Agent, or Firm* — Eversheds Sutherland (US) LLP

(57) ABSTRACT

An activated carbon monolith catalyst comprising a finished self-supporting activated carbon monolith having at least one passage therethrough, and comprising a supporting matrix and substantially discontinuous activated carbon particles dispersed throughout the supporting matrix and at least one catalyst precursor on the finished self-supporting activated carbon monolith. A method for making, and a method for use, of such an activated carbon monolith catalyst in catalytic chemical reactions are also disclosed.

22 Claims, 1 Drawing Sheet

ACTIVATED CARBON MONOLITH CATALYST, METHODS FOR MAKING SAME, AND USES THEREOF

CROSS-REFERENCE TO RELATED APPLICATIONS

This application is a divisional of U.S. application Ser. No. 11/102,452, filed Apr. 8, 2005, which is incorporated herein by reference in its entirety.

FIELD OF THE INVENTION

The present invention relates generally to catalytic structures, methods for making same, and uses thereof. In particular, this invention relates to activated carbon monolith catalysts and methods for making and using them.

BACKGROUND OF THE INVENTION

Carbon catalysts play an important role in various chemical processes from industrial to pharmaceutical settings. Carbon catalysts enable chemical reactions to occur much faster, or at lower temperatures, because of changes that they induce in the reactants. Carbon catalysts may lower the energy of the transition state of chemical reactions, thus lowering the activation energy. Therefore, molecules that would not have had the energy to react, or that have such low energies that it is likely that they would take a long time to do so, are able to react in the presence of a carbon catalyst by reducing the energy required for the reaction to occur. Not only do carbon catalysts increase the rate of reaction, but they may also drive a reaction towards the desired product.

Typically, catalysts are applied to a substrate before introduction to a chemical process. Desirably, the substrate holds the catalyst while presenting the catalyst to reactants in the chemical process. Conventional catalyst substrates, or supports, include carbon or ceramic granules arranged in a bed, and ceramic monoliths.

Traditionally, carbons utilized as catalyst supports are either granules or powders. In a perfect world, carbons used for catalyst supports would be chosen only for their activity and selectivity. The more common features that are important factors in determining activity and selectivity are surface area, pore volume, pore size, ash content, friability, availability, and/or other elements contained in the carbon matrix. The foregoing are not the only desirable features; rather, they are ones that are known to be obtainable within the art.

Conventionally, carbon catalyst supports are chosen more for properties that meet parameters of the chemical process, than for features that would make purely the best catalyst, for highest activity and selectivity. While a particular carbon substrate might have the best features for activity and selectivity, it may not be the best choice considering the chemical process parameters. For example, carbon granules suffer from attrition making exact pressure drop determinations difficult, and they scale up poorly in chemical processes. When chemical reactants trickle through a bed of granular carbon catalyst, the catalyst must be as attrition resistant as possible, less the bed collapse and flow cease or the catalyst metals be lost. Attrition is a particularly aggravating issue, because it alters the physical parameters of the chemical process as it proceeds, and causes financial loss, particularly when the catalyst is a precious metal. For this reason, carbons of choice are typically nutshell carbons, which are durable, but which have very small pores that can harshly limit activity and selectivity. When a powder carbon catalyst is stirred violently in a batch reactor with chemical reactants, the carbon catalyst must be non-friable to some degree to allow it to be economically separated from the reaction at termination in order to prevent loss of the catalyst. Thus, perhaps one must exclude carbons with better catalytic properties, but which are too friable.

Ceramic catalytic monoliths have been used in the art for advantages they provide over fixed bed supports, such as predictable pressure drop through the catalyst bed, scalability based on a model that predicts performance through incremental increases in volume of catalyst with respect to the same reactant volume flow, separation of the catalysts from the reaction and from the product stream, practical continuous operation and ease of replacement of the catalyst, and layering of the catalyst or the catalysts either on the monoliths' wall depth or wall length, or both. The low pressure drop of catalytic monoliths' allows them to operate at higher gas and liquid velocities. These higher velocities of gas and liquids promote high mass transfer and mixing.

Catalytic monolith development has been an ongoing process in an effort to enhance catalytic activity, catalytic selectivity, and catalyst life. Although monoliths have advantages over fixed bed supports, there are still problems associated with traditional ceramic monoliths. Exposure of the catalytic metal in the catalytic monolith to the reactants is necessary to achieve good reaction rates, but efforts to enhance exposure of the catalytic metal often have been at odds with efforts to enhance adhesion of the metal to the monolith substrate. Thus, catalytic ceramic monoliths have fallen short of providing optimal catalytic selectivity and activity.

As seen below, ceramic carbon catalyst monoliths developed to date, on one hand may provide good selectivity and activity, but on the other hand may not be suitable for process parameters such as durability and inertness. Conversely, ceramic carbon catalyst monoliths suitable for such process parameters may have diminished selectivity and activity. Thus, it would be ideal to take a carbon with the best features for a catalyst based on its activity and selectivity, and then form a carbon monolith catalyst to flit the process parameters of choice.

There have been efforts to form a carbon support that would have some of the features of a ceramic monolith catalyst. These efforts fall into three general classes: gluing or binding of carbon granules or powder to form larger structures, coating ceramic monoliths with an organic compound such as sugars or liquid polymer plastics, followed by carbonization of the organic compound on the ceramic monolith, and formation of a structure from an organic material, such as a plastic or nylon, followed by carbonization of the structure.

The binding of carbons gives some degree of choice of carbon precursor, but the result is a carbon support with the binder as a new element. These binders can vary from organic glues to pitches. In most cases, the binders are susceptible to attack by the reaction media in application. Some cause side reactions, or poison the catalyst. Furthermore, the result is a random binding of granules, or the creation of a new granule—a chopped extrudate of powdered carbon and binder. In either case, the parameters of flow are not predictable by simple, understandable models. Although the carbons selected have generally been in use as unbound catalyst supports, and unbound activity and selectivity information on the carbon can sometimes be used, still the binder is not inert, and therefore binder influence is always an issue.

Carbonization of an organic material forms a support with little hope of prior carbon activity or selectivity information. Because the carbon is formed each time the support is prepared, and is limited to those precursor and organic materials that can be coated or formed and carbonized, commercially available carbons, known in the art to produce excellent catalyst, are excluded from consideration. Furthermore, the carbons normally used in preparation of catalyst supports are prepared from naturally occurring materials such as wood, peat, nutshell, and coal, and not from refined or organic chemicals. Carbon produced from naturally occurring material is known to retain some of the beneficial structural characteristics as well chemical nature of the precursor material. These characteristics are known to be important to the final activity and selectivity of the catalyst. While carbonization may be a way of producing a carbon coating or structure, it extends marginally the catalyst art, and does not produce a catalyst utilizing the known carbon methods of choice in the art.

Thus, there is a need in the art for a carbon monolith catalyst, and a process for making the same, having attrition resistance, predictable pressure drop, high selectivity, high activity, and scalability for commercial economy and efficiency. More particularly, there is a need in the art to provide an activated carbon monolith catalyst which allows the manufacture of the catalyst of choice to fit the process parameters, while increasing the utility of the catalyst with predictable pressure drop through the catalyst bed, scalability based on a model that predicts performance through incremental increases in volume of catalyst with respect to the same reactant volume flow, separation of the catalysts from the reaction and from the product stream, practical continuous operation and ease of replacement of the catalyst, and layering of the catalyst or the catalysts either on the monolith's wall depth or wall length, or both, and while providing high selectivity and activity.

SUMMARY OF THE INVENTION

Objects and advantages of the invention will be set forth in part in the following description, or may be obvious from the description, or may be learned through practice of the invention. Unless otherwise defined, all technical and scientific terms and abbreviations used herein have the same meaning as commonly understood by one of ordinary skill in the art to which this invention pertains. Although methods and compositions similar or equivalent to those described herein can be used in the practice of the present invention, suitable methods and compositions are described without intending that any such methods and compositions limit the invention herein.

The present invention addresses the above-described need by providing an activated carbon monolith catalyst comprising a finished self-supporting activated carbon monolith having at least one passage therethrough, and comprising a supporting matrix and substantially discontinuous activated carbon particles dispersed throughout the supporting matrix, and at least one catalyst precursor supported on the finished self-supporting activated carbon monolith. The supporting matrix holds the activated carbon particles in a monolithic form. In preferred embodiments, the supporting matrix comprises a ceramic or another substantially inert material such as carbon.

The activated carbon monolith catalyst of this invention is not limited to use of precursor materials that must be carbonized to form a carbon catalyst support. It can include any activated carbon particles from any source. Thus, the activated carbon monolith catalyst of this invention can be made with activated carbon particles chosen for their superior activity and selectivity for a given application. The activated carbon monolith catalyst can then be expected to have a predictable activity and selectivity based on the knowledge available regarding the particular activated carbon particles used. In addition, the activated carbon particles in the activated carbon monolith catalyst of this invention are dispersed throughout the structure of the catalyst, giving depth to the catalyst activity and selectivity. The activated carbon particles are bound by a supporting matrix, which desirably is an inert binder and is not susceptible to attack by reaction media. Furthermore, the activated carbon monolith catalyst of this invention exhibits the desirable features of a ceramic monolith, while also presenting the advantage of a choice of a wide variety of particulate carbon substrates. Such desirable features include ease of separation of the catalyst from a product in a chemical reaction, and predictable fluid flow, among others. Because the activated carbon particles are fixed in a monolithic form, regions of the monolith, in particular embodiments, can include different catalysts as desired. Such regions would not migrate in monolithic form as they would with loose activated carbon particles.

Accordingly, with the activated carbon monolith catalyst of this invention, the catalyst can be chosen based on its superior activity and selectivity, while pressure drop through the monolith is predictable, processes using the activated carbon monolith catalyst are scalable based on a model that predicts performance through incremental increases in volume of catalyst with respect to the same volume flow, and the catalyst is separable from the reaction and product streams. The activated carbon monolith catalyst is useful in continuous operations which were formerly practical only in batch processes; the activated carbon monolith catalyst is easy to replace, and the catalyst precursor can be layered either on the carbon monolith catalyst wall depth or wall length, or both. The activated carbon monolith catalyst of this invention can be used in continuous processes because a process stream can flow through it. Due to the low pressure drop through the activated carbon monolith catalyst of this invention, continuous processes can operate at high velocities.

In another embodiment of the present invention, a method for making an activated carbon monolith catalyst is provided comprising providing a finished self-supporting activated carbon monolith having at least one passage therethrough and comprising a supporting matrix and substantially discontinuous activated carbon particles dispersed throughout the supporting matrix and applying at least one catalyst precursor to said finished extruded activated carbon monolith.

In another embodiment of the present invention, a method for catalytic chemical reaction is provided comprising contacting at least one reactant with an activated carbon monolith catalyst comprising (a) a finished self-supporting extruded activated carbon monolith having at least one passage therethrough and comprising a supporting matrix and substantially discontinuous activated carbon particles dispersed throughout the supporting matrix, and (b) at least one catalyst precursor on said finished extruded activated carbon monolith.

Other objects, features, and advantages of this invention will become apparent from the following detailed description of embodiments, drawings, and claims.

Figure 1:
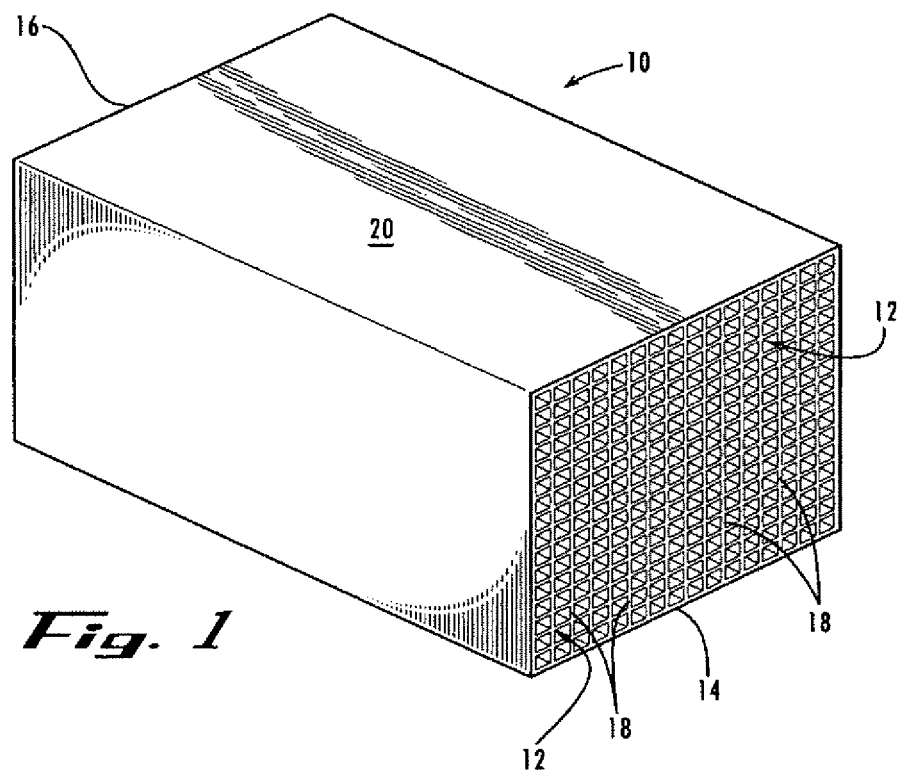
FIG. 1 is a perspective view of an activated carbon monolith catalyst made in accordance with an embodiment of the invention.

In describing the proffered embodiment of the invention, which is illustrated in the drawings, specific terminology will be resorted to for the sake of clarity. However, it is not intended that the invention be limited to the specific terms so selected, and it is to be understood that each specific term includes all technical equivalents which operate in a similar manner to accomplish a similar purpose.

DETAILED DESCRIPTION OF EMBODIMENTS

Reference now will be made in detail to the presently proffered embodiments of the invention, one or more examples of which are illustrated in the accompanying drawings. Each example is provided by way of explanation of embodiments of the invention, not limitation of the invention. In fact, it will be apparent to those skilled in the art that various modifications and variations can be made in the present invention without departing from the spirit or scope of the invention. For instance, features illustrated or described as part of one embodiment, can be used on another embodiment to yield a still further embodiment. Thus, it is intended that the present invention cover such modifications and variations within the scope of the appended claims and their equivalents.

As summarized above, this invention encompasses an activated carbon monolith catalyst comprising a finished self-supporting activated carbon monolith having at least one passage therethrough, and comprising a supporting matrix and substantially discontinuous activated carbon particles dispersed throughout the supporting matrix, and at least one catalyst precursor on the finished self-supporting activated carbon monolith. A method for making an activated carbon monolith catalyst, and application of the activated carbon monolith catalyst in chemical processes, are also disclosed. Embodiments of this invention are described below, beginning with the structure and components of the activated carbon monolith catalyst, followed by methods of making and using the activated carbon monolith catalyst.

Carbon Monolith Catalyst Structure

As used herein, the term "activated carbon monolith catalyst" refers to a combination of an activated carbon monolith substrate and at least one catalyst precursor. The term "catalyst" means a material that is present in a reaction, adjusts the activation energy of the reaction and provides some reaction selectivity, but is not consumed in the reaction. The term "catalyst precursor" means a material that is capable of creating a catalytically active site on a substrate material. A catalyst precursor may or may not undergo a change in becoming catalytically active.

Suitable catalyst precursors are selected from precious metal, base metal, or a combination thereof. Non-limiting examples of precious metals include, but are not limited to, palladium, platinum, rhodium, ruthenium, iridium, osmium, silver, and gold. The precious metal may also be reduced precious metal, precious metal oxide, precious metal sulfide, precious metal with modifiers, or a combination thereof. Non-limiting examples of modifiers include, but are not limited to, potassium, calcium, magnesium, sodium hydrated oxides, and sodium hydroxides. Non-limiting examples of base metal include, but are not limited to, zinc, nickel, copper, manganese, iron, chromium, vanadium, molybdenum, and combinations thereof. Base metal may also be present as oxides, hydrated oxides, carbonates, sulfides, or a combination thereof. An illustrative example of the combination of catalyst precursors may be a solution of palladium chloride and sodium carbonate, to be combined with an activated carbon monolith to form an activated carbon monolith catalyst.

FIG. 1 illustrates an activated carbon monolith catalyst 10 made according to an embodiment of the present invention. The activated carbon monolith catalyst 10 comprises a finished self-supporting activated carbon monolith and at least one catalyst precursor applied to the monolith. As used herein, the phrase "finished self-supporting activated carbon monolith" refers to a solid-phase material comprising activated carbon without any catalyst precursor yet added to the monolith. The activated carbon monolith catalyst 10 shown in FIG. 1 comprises an activated carbon monolith having a honeycomb shape and comprising activated carbon particles, ceramic forming material, flux material, and water, to which at least one catalyst precursor has been applied. The activated carbon monolith catalyst has a plurality of passages 12 extending through the monolith from a frontal end 14 to a rearward end 16. The passages 12 are substantially square in cross section, linear along their length, and formed by surrounding walls 18, however, the passages can have other cross-sectional shapes such as rectangular, round, triangular, hexagonal, oval elliptical, and the like. The passages 12 are encased by an outer skin 20 of the monolith.

The activated carbon particles in the activated carbon monolith catalyst 10 are dispersed throughout the supporting matrix, giving depth to the catalyst activity and selectivity. The activated carbon particles are bound by the supporting matrix, which desirably is an inert binder and is not susceptible to attack by reaction media. In the embodiment shown in FIG. 10, the supporting catalyst is a ceramic, but other materials can be used as the supporting matrix. For example, a mixture of activated carbon particles and a polymer resin, such as a thermoplastic polymer, can be formed into a monolith and pyrolyzed to convert the resin into a carbon matrix.

In one embodiment of the present invention, the activated carbon monolith catalyst 10 comprises a total catalyst precursor on the finished activated carbon monolith in an amount from about 0.01 percent to about 5.0 percent by weight of the activated carbon monolith catalyst. The preferred range depends on the application of the metal of choice. For example, with precious metal loading, the total catalyst precursor on the finished extruded activated carbon monolith may be in an amount from about 0.01 percent to about 1.0 percent by weight of activated carbon monolith catalyst. In another example, with base metal loading, the total catalyst precursor on the finished extruded activated carbon monolith may be in an amount from about 1.0 percent to about 5.0 percent by weight of activated carbon monolith catalyst.

The activated carbon monolith catalyst is porous, with pores extending into the depths of the monolith walls. Because the activated carbon particles are substantially discontinuous and are dispersed throughout the ceramic matrix, it is possible, depending on the catalyst precursor and the conditions under which the catalyst precursor is applied to the monolith, for the catalyst precursor to be present on the exterior surface of the monolith walls, and into the depths of the monolith walls via passageways between the discontinuous activated carbon particles, via passageways between the ceramic matrix and the carbon particles, and via pores in the carbon particles themselves. Placement of the catalyst precursor within the monolith structure can be controlled by selection of catalyst precursor, and variation in parameters of catalyst precursor application such as temperature, ionic strength of catalyst precursor solution, duration of catalyst precursor application, pH of the catalyst precursor solution, and the like. The catalyst precursor therefor is desirably disposed on the surface of the finished self-supporting activated carbon monolith, such surface including area on the exterior walls of the monolith as well as area within passageways and pores in the depth of the monolith walls.

Figure 2:
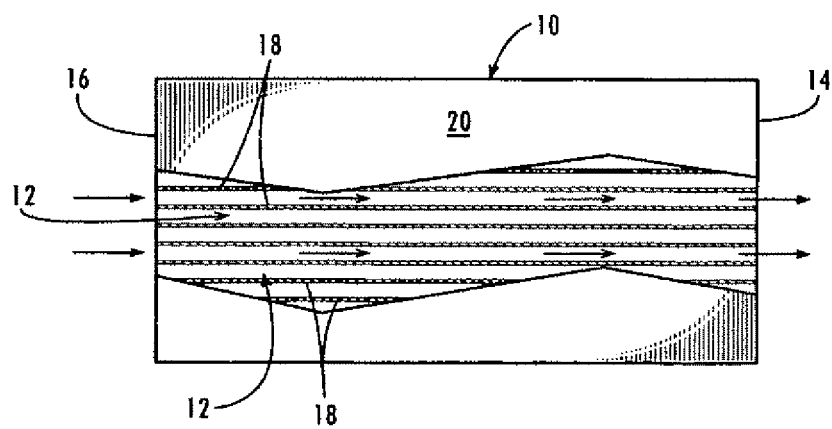
FIG. 2 is a partial side elevation of an activated carbon monolith catalyst of FIG. 1 with a portion of the skin removed to illustrate the flow of fluid through the honeycomb passages of the monolith.

As will be discussed in more detail below, the activated carbon monolith catalyst 10 is useful in a variety of chemical processes FIG. 2 illustrates the flow of fluid through the passages 12 in the activated carbon monolith catalyst 10. A catalyst precursor applied on and within the walls of the monolith structure, becomes catalytically active, and catalyzes a chemical reaction as reactants flow through the monolith.

Method of Making the Activated Carbon Monolith Catalyst

Generally described, the activated carbon monolith catalyst 10 is made by providing a finished self-supporting activated carbon monolith and applying at least one catalyst precursor to the finished activated carbon monolith. According to a preferred embodiment, the finished activated carbon monolith is formed by mixing together activated carbon, ceramic forming material, flux material, and water to make an extrudable mixture, wherein binder is optionally added. The extrudable mixture is extruded through an extrusion die to form the monolith having a honeycomb structure. It is appreciated that the finished extruded activated carbon monolith may be a honeycombed structure, or any other structure which is capable of being made by the extrusion process. After extrusion, the extruded honeycomb monolith retains its shape while it is dried and then fired at a temperature and for a time period sufficient to react or fuse the ceramic forming material together and form a ceramic matrix, having activated carbon particles dispersed throughout the ceramic matrix or structure, and exhibiting sufficient strength for its intended end use. At least one catalyst precursor is thereafter applied to the finished extruded activated carbon monolith.

Alternatively to extruding an extrudable mixture to form a finished self-supporting activated carbon monolith, such monoliths can be formed by pressing a suitable activated carbon and binder mixture with a die or press, or by drawing a suitable mixture through a die with a suitable drawing force. For example, a mixture of activated carbon particles and a polymer resin, such as a thermoplastic polymer, can be pressed or drawn to form a monolith and pyrolyzed to convert the resin into a carbon matrix.

The application of catalyst precursor to the finished activated carbon monolith may be achieved according to any method known to those of ordinary skill in the art. In one embodiment of the present invention, the finished activated carbon monolith is contacted with a solution comprising at least one catalyst precursor, such as for example, a palladium chloride solution. The solution comprising at least one catalyst precursor, hereinafter is referred to as "catalyst precursor solution", is contacted with the finished activated carbon monolith at a controlled or timed rate. "Controlled" or "timed rate" refers to the addition of the catalyst precursor solution, or other components of the coating process, at a defined rate which achieves the desired contact of the catalyst precursor to the finished activated carbon monolith. "Defined rate" refers to any rate which is capable of being reproduced or recorded. For example, the "controlled" or "timed rate" may be defined as a rate of catalyst precursor solution or other coating component addition at about 0.5 cc/second/gram of finished activated carbon monolith to about 50 cc/second/gram of finished activated carbon monolith. In another example, the timed rate may be 0.5 cc/minute/gram of finished activated carbon monolith to about 100 cc/minute/gram of finished activated carbon monolith.

It is appreciated that one of ordinary skill in the art may vary the time or volume increments of the addition of the catalyst precursor solution to achieved the desired catalyst precursor application process. For example, the catalyst precursor solution may be added to the finished activated carbon monolith at a timed rate of 15.0 cc every 6.0 seconds for a 6.0 gram finished activated carbon monolith. The catalyst precursor solution is added for a period of time which will achieve an activated carbon monolith catalyst comprising a total weight of the catalyst precursor in the amount of about 0.01% to about 5.0% by weight to the total weight of the activated carbon monolith catalyst. It is appreciated that the time period will depend on the concentration of the catalyst precursor solution, and the controlled rate of addition of the catalyst precursor solution. For example, the addition of the catalyst precursor solution may last from about 10.0 minutes to about 1.0 hour.

In a sub-embodiment of the present invention, the catalyst precursor application process also comprises other components such as water, buffering agent, optional reducing agent, and optional hydrogen peroxide, optional base, and optional acid. The water preferably is deionized. As used herein "buffering agent" refers to any compound which resists changes in pH upon the addition of small amounts of either acid or base. A buffering agent comprises a weak acid or base and its salt. Non-limiting examples of a buffering agent include, but are not limited to, sodium carbonate, potassium carbonate, sodium hydroxide, potassium hydroxide, and sodium bicarbonate. As used herein, "reducing agent" refers any substance that can donate electrons to another substance or decrease the oxidation numbers in another substance. Non-limiting examples of reducing agent include, but are not limited to, sodium formate, potassium formate, hydrogen, sodium borohydride, sodium hypophosphite, hydrazine, and hydrazine hydrochloride. It is appreciate to those of ordinary skill in the art that not all metals such as base metals require a reducing agent.

In yet another sub embodiment, the chlorides of some metals, usually base metals, are soluble alone in water. Others, such as platinum or palladium, require hydrochloric acid, or being pan of a potassium or sodium chloride compound for improved solubility. For example, palladium chloride may be dissolved in hydrochloric acid. In another example, sodium chloropalladite is formed by adding sodium hydroxide to palladium chloride dissolved in hydrochloric acid. Other chemical combinations to improve the solubility of the catalyst precursor are known in the art.

The temperature of the catalyst precursor solution may be from about 30.0° C. to about 75.0° C. In another example, the temperature may be from about 50.0° C. to about 65.0° C. Preferably the temperature is at 65.0° C.

The catalyst precursor solution is usually acidic. For example, the pH of the catalyst precursor solution may range from about 1.0 to about 6.9. In another example, the pH of the catalyst precursor solution may range from about 4.0 to about 6.5. The catalyst precursor application process may be carried out in an environment wherein the pH may range from about 1.0 to about 13.0 depending on the equipment and reagents utilized. It is appreciated that equipment such as stainless steel equipment (i.e. acid reactive equipment) requires a coating process environment wherein the pH is basic to avoid deterioration of the equipment. Alternatively, glass or glass-lined equipment may be suitable when using an acidic environment for the catalyst precursor application.

In another embodiment, the method for making the activated carbon monolith catalyst 10 includes first mixing the dry ingredients of the extrudable mixture and then adding the liquid ingredients to the dry mixture; however, the order in which the ingredients are added to the extrudable mixture can be varied by alternating mixing of dry and liquid ingredients as long as the proper amount of moisture is added to make an extrudable mixture which holds its shape during and after extrusion. A suitable finished activated carbon monolith is disclosed in U.S. Pat. No. 5,914,294, the disclosure of which is expressly incorporated herein by reference.

The activated carbon is desirably present in the extrudable mixture in an amount from about 20 to about 70 parts, by weight, and more desirably, in an amount from about 30 to about 50 parts, by weight. A variety of activated carbons can be used in this invention. The activated carbon surfaces adsorb volatile organic compounds and other chemical agents. The most suitable activated carbon will depend on the intended application, particularly the nature of the material to be adsorbed. Thus, the physical properties of the activated carbon, such as the surface area and the pore structure, may be varied depending on the intended application. Desirably, the activated carbon has a nitrogen B.E.T. surface from about 600 to about 2000 $m^2/g$. More desirably, the activated carbon has a nitrogen B.E.T. surface from about 800 to about 1800 $m^2/g$, and even more desirably has a nitrogen B.E.T. surface from about 1000 to about 1600 $m^2/g$. Suitable activated carbon can also be characterized by having a particle size such that more than 40% by weight of the activated carbon passes through a 200 mesh screen, and more desirably, by having a particle size such that more than 65% by weight of the activated carbon passes through a 200 mesh screen.

Activated carbon suitable for use in the present invention may be made from a variety of precursors including bituminous coal, lignite, peat, synthetic polymers, petroleum pitch, petroleum coke, coal tar pitch, and lignocellulosic materials. Suitable lignocellulosic materials include wood, wood dust, wood flour, sawdust, coconut shell, fruit pits, nut shell, and fruit stones. Suitable commercially available activated carbons include Nuchar® activated carbon available from Westvaco Corporation of New York, N.Y., Acticarbone® carbon available from Ceca SA of Paris, France, and Darco® carbon and Norit® carbon available from Norit-Americas of Marshall, Tex.

The ceramic forming material is present in the extrudable mixture in an amount from about 20 to about 60 parts, by weight and more desirably, in an amount from about 30 to about 50 parts, by weight. The term ceramic forming material means alumina/silicate-based material which, upon firing, is capable of reacting together with other ingredients to form a high strength, crystal/glass mixed-phase ceramic matrix. In this application, the reacted ceramic material provides a matrix for supporting the activated carbon, and has sufficient strength to withstand handling and use of the monolith in the intended application and maintain its intended shape without cracking or otherwise disintegrating. The ceramic forming material desirably includes a substantial portion of moldable material which is plastic in nature and thus, when mixed with liquid, can be molded or extruded into a shape and will maintain that shape through drying and firing. Such a suitable plastic or moldable material is ball clay. A particularly suitable commercially available ball clay is OLD MINE #4 ball clay available from Kentucky-Tennessee Clay Company of Mayfield, Ky. Other suitable plastic-like ceramic forming materials include, but are not limited to, plastic kaolins, smectite clay minerals, bentonite, and combinations thereof. Bentonite and smectites are desirably used in combination with ball clay or kaolin.

The ceramic forming material also desirably includes a filler material which is non-plastic and reduces shrinkage of the monolith during the steps of drying and firing. A non-limiting example of a suitable ceramic filler is calcined kaolin clay. A particularly suitable commercially available calcined kaolin clay is Glomax LL available from Georgia Kaolin Company, Inc. of Union, N.J. The filler desirably is present in the extrudable mixture in an amount up to about 15 parts, by weight, and more desirably, from about 1 to about 15 parts, by weight, and even more desirably, from about 3 to about 10 parts, by weight. Other suitable filler materials include, but are not limited to, calcined kyanite, mullite, cordierite, clay grog, silica, alumina, and other calcined or non-plastic refractory ceramic materials and combinations thereof.

The flux material is present in the extrudable mixture in an amount from about 4 to about 20 parts, by weight, and aids in forming the ceramic bond between the ceramic forming materials by causing the ceramic forming material particles to react together and form a ceramic matrix at a lower firing temperature than if the flux material were not present. More desirably, the flux material is present in the extrudable mixture in an amount from about 4 to about 10 parts, by weight. Suitable flux materials include, but are not limited to, feldspathic materials, particularly nepheline syenite and feldspar, spodumene, soda, potash, sodium silicate, glass frits, other ceramic fluxes, and combinations thereof. A particularly desirable commercially available flux material is MINEX®7 nepheline syenite available from Unimin Specialty Materials, Inc. of Elco, Ill.

The binder is present in the extruded mixture in an amount from about 0.5 to about 9 percent, by weight, based on the solids content of the binder, and enhances the strength of the monolith after extrusion so that the extruded monolith maintains its shape and integrity after extrusion and through drying and firing. The binder is desirably present in the extruded mixture in an amount from about 2 to about 7 percent, by weight, based on the solids content of the binder. A particularly suitable binder is methylcellulose, and a suitable commercially available methylcellulose is METHOCEL A4M methylcellulose available from Dow Chemical Company of Midland, Mich. Desirably, methylcellulose is present in the extrudable mixture in an amount from about 0.5 to about 9 parts, by weight, of the extrudable mixture, and more desirably, from about 2 to about 7 parts, by weight. Another suitable binder, used in combination with methylcellulose, is an acrylic binder. Examples of such polymers are JONREZ D-2106 and JONREZ D-2104 available from Westvaco Corporation of New York, N.Y., and Duramax acrylic binder which is available from Rohm & Haas of Montgomeryville, Pa. The acrylic polymer, having a medium to high glass transition temperature is desirably present in an amount from zero up to about 4 parts, by weight, of the extrudable mixture, based on the solids content of the acrylic binder. Other suitable binders include hydroxypropyl methylcellulose polymers, CMC, polyvinyl alcohol, and other temporary binder/plasticizer additives.

Another desirable component of the extrudable mixture is sodium silicate, which increases the strength of both the dry, but unfired monolith and the fired monolith, and is a flux material. The sodium silicate is thus both a binder when the monolith is in the dry state and a flux material, and is added to the extrudable mixture as a solution. The sodium silicate is desirably present in the extrudable mixture in an amount up to about 7 parts, by weight, based on the solids content of the sodium silicate, and more desirably in an amount from about 0.0 to about 7 parts, by weight, based on the solids content of the sodium silicate. A suitable commercially available sodium silicate solution is a 40% solids, Type N solution, available from PQ Corporation, Industrial Chemicals Division, Valley Forge, Pa. Other suitable binders for the dried monolith include silica sol and alumina sol.

The extrudable mixture includes water in an amount sufficient to make an extrudable mixture and desirably includes from about 60 to about 130 parts water, by weight of dry ingredients. Preferably, the water is chilled before it is added to the mixture and more preferably is added to the system at or near 0° C. This low temperature helps keep the ingredients cool during mixing, and helps to overcome any exotherm which may occur as a result of mixing the ingredients, or as a result of heating of the mixture, which occurs as a result of the mechanical action of mixing.

The extrudable mixture is formed into a shape, which will be the shape of the finished self-supporting activated carbon monolith, by passing the extrudable mixture through an extrusion die. The finished self-supporting activated carbon monolith usually has a block or cylindrical shape, and includes at least one passageway along its length and desirably includes a plurality of passageways extending along the length of the finished self-supporting activated carbon monolith. The activated carbon monolith catalyst is designed to be placed in a stream of a fluid containing one or more chemical reactants, such that the fluid is forced through the passages in the monolith. Ideally, the amount of internal surface area of the activated carbon monolith catalyst exposed to the fluid is designed to maximize the efficiency of the catalytic reaction. A honeycomb-shaped structure is preferred for the finished self-supporting activated carbon monolith. Honeycomb extruders are known in the art of ceramics and have been used to produce ceramic monoliths.

Desirably, the honeycomb structure of the finished self-supporting activated carbon monolith has an open frontal area greater than 50 percent and up to about 85 percent, and desirably about 74 percent, after drying and firing. The open frontal area of the monolith is the percentage of open area of the monolith taken across a plane substantially perpendicular to the passageway length of the monolith. Furthermore, the finished self-supporting activated carbon monolith desirably has a honeycomb pattern with square cells and about 540 cells per square inch. The honeycomb structure desirably has a cell-to-cell pitch of about 0.043 inches, a cell wall thickness of about 6 mils, and an open frontal area of about 0.0014 square inches per cell. More broadly, for a variety of applications, the cell density may vary from 1 to 900 cells per square inch or higher, with the cell wall thickness ranging from about 150 mils to about 4 mils, and the cell-to-cell pitch varying from about 1 to about 0.033 inches.

The extruded activated carbon honeycomb monolith is dried in a manner so as to prevent cracking of the structure. To alleviate cracking, the extruded carbon honeycomb monolith is dried so that water is removed at substantially the same rate throughout the carbon honeycomb monolith. Suitable drying methods include dielectric drying, microwave drying, warm air drying with the monolith wrapped in plastic or wet cloths, vacuum drying, freeze drying, and humidity control drying.

After drying, the dried extruded activated carbon honeycomb monolith is fired at a temperature from about 1600 to about 1950° F. and desirably from about 1850 to about 1950° F., in a nitrogen or other non-oxidizing or slightly reducing atmosphere. The activated carbon honeycomb monolith should be fired at a temperature sufficient to react the ceramic forming materials together to create a matrix for holding the activated carbon and maintaining the honeycomb shape of the extrusion. The bonds created by the firing should be sufficient to create a matrix having a strength able to withstand handling and use of the carbon monolith catalyst in intended applications. The relatively high surface area of the material forming the finished self-supporting activated carbon monolith makes it desirable as a catalyst support. As explained above, the finished self-supporting activated carbon monolith is porous, and catalyst precursor can be applied on the exterior of the monolith and through the depth of the monolith via pores and passages in the monolith walls.

In a desired embodiment, the finished self-supporting activated carbon monolith is made by extruding a mixture comprising: 30 parts, by weight, activated carbon; 50 parts, by weight, ball clay; 10 parts, by weight, calcined kaolin clay; 10 parts, by weight, nepheline syenite; 2.5 parts, by weight, methylcellulose; 2.8 parts, by weight, sodium silicate solids; and 75 parts, by weight, water. The resulting finished self-supporting activated carbon monolith has a high structural integrity, exhibiting axial crushing strength of about 1500 psi and a modulus of rupture (MOR) of about 150 psi in the axial direction.

It should be understood that the activated carbon monolith catalyst of this invention could be used in a variety of applications owing to the wide range of carbon content which the carbon monolith catalysts can contain. For example, crushing strengths of the finished self-supporting activated carbon monolith will vary depending on the relative amounts of carbon and ceramic forming material, the firing temperature, and the particle size of the ingredients. In particular embodiments, the finished self-supporting activated carbon monolith may include activated carbon particles in an amount from about 20 to about 95% by weight of the finished self-supporting activated carbon monolith, preferably in an amount from about 20 to about 80% by weight of the finished self-supporting activated carbon monolith, and more preferably in an amount from about 30 to about 50% by weight of the finished self-supporting activated carbon monolith. The higher loading of carbon (greater then 80% by weight) is more effectively achieved with a non-ceramic matrix such as carbon. The axial crushing strength of the finished self-supporting activated carbon monolith desirably ranges from 500 to 1600 psi.

Catalytic Reactions

In another embodiment of the present invention, a method for catalytic chemical reaction is provided comprising contacting at least one reactant with an activated carbon monolith catalyst comprising (a) a finished self-supporting activated carbon monolith having at least one passage therethrough, and comprising a supporting matrix and substantially discontinuous activated carbon particles dispersed throughout the supporting matrix, and (b) at least one catalyst precursor on the finished activated carbon monolith.

The term "reactant" as used herein refers to any chemical compound in which a catalyst can affect a chemical reaction by increasing the reaction rate, and/or lowering the activation energy, and/or create a transition state of lower energy when the chemical compound is alone, in combination with another chemical compound, or in combination with at least two chemical compounds of the same species.

The carbon monolith catalyst of the present invention is suitable for various catalytic reactions. "Catalytic reaction" or "reaction" as used herein refers to heterogeneous and homogeneous catalytic reaction.

Heterogeneous catalytic reaction involves the use of a catalyst in a different phase from the reactants. Typical examples involve a solid catalyst with the reactants as either liquids or gases, wherein one or more of the reactants is adsorbed onto the surface of the catalyst at active sites. Homogeneous catalytic reaction, on the other hand, involves the use of a catalyst in the same phase as the reactants.

In one embodiment, nitrobenzene is passed through the activated carbon monolith catalyst comprising palladium, and under hydrogen pressure. The result is the production of aniline.

In another embodiment, phenol is passed through the activated carbon monolith catalyst comprising palladium doped with sodium, and under hydrogen pressure. The result is the production of cyclohexanone.

In yet another embodiment, crude terephthalic acid containing such color bodies as 4-carboxybenzaldehyde is passed through the activated carbon monolith catalyst comprising palladium, and under hydrogen pressure. The result is the production of purified terephthalic acid with very few color bodies present.

In yet a further embodiment, hydrogen and nitrogen are passed through the activated carbon monolith catalyst comprising ruthenium, and under pressure and heat. The result is the production of ammonia.

In another embodiment, carbon monoxide or carbon dioxide is passed through the activated carbon monolith catalyst comprising ruthenium, and under hydrogen pressure and heat. The result is a hydrocarbon, Fisher-Tropsch Synthesis.

In yet another embodiment, hydrocarbon and water are passed through the activated carbon monolith catalyst comprising ruthenium. This process is also known as steam cracking. The result is hydrogen and carbon monoxide, wherein the hydrogen may be used in a fuel cell.

In yet another embodiment, Nitrobenzene is passed through the activated carbon monolith catalyst comprising platinum, and under hydrogen pressure. The result is the production of aniline.

In another embodiment, hydrogen and oxygen are passed through the activated carbon monolith catalyst comprising platinum, in a fuel cell. The result is electricity.

In another embodiment, amine and aldehyde or ketone are passed through the activated carbon monolith catalyst comprising sulfided platinum, and under hydrogen pressure. The result is a reductive alkylation product.

In another embodiment, nitrobenzene is passed through the activated carbon monolith catalyst comprising sulfided platinum, and under hydrogen pressure. The result is a hydroxyl amine.

In another embodiment, aniline is passed through the activated carbon monolith catalyst comprising rhodium, and under hydrogen pressure. The result is the cyclohexylamine.

In another embodiment, phenol is passed through the activated carbon monolith catalyst comprising rhodium and under hydrogen pressure. The result is cyclohexanol.

In another embodiment, gas phase catalytic reaction may also be achieved with the activated carbon monolith catalyst of the present invention. Non-limiting examples include:

Oxidation

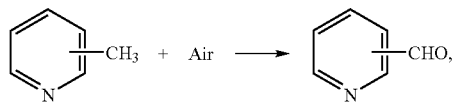

Ammoxidation

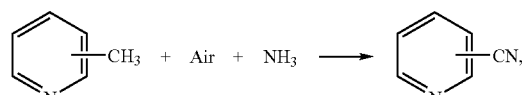

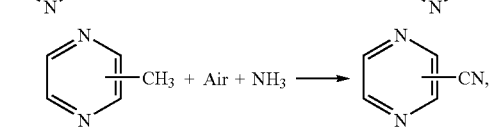

Dehydration

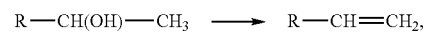

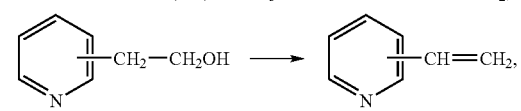

Dehydrogenation

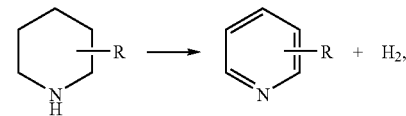

Cyclic-Condensation and Dehydrogenation, Heterocyclic Compounds Synthesis

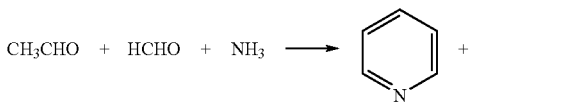

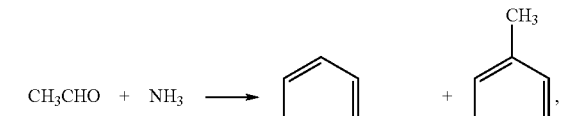

Alkylation

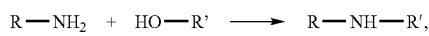

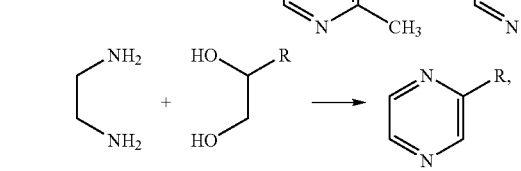

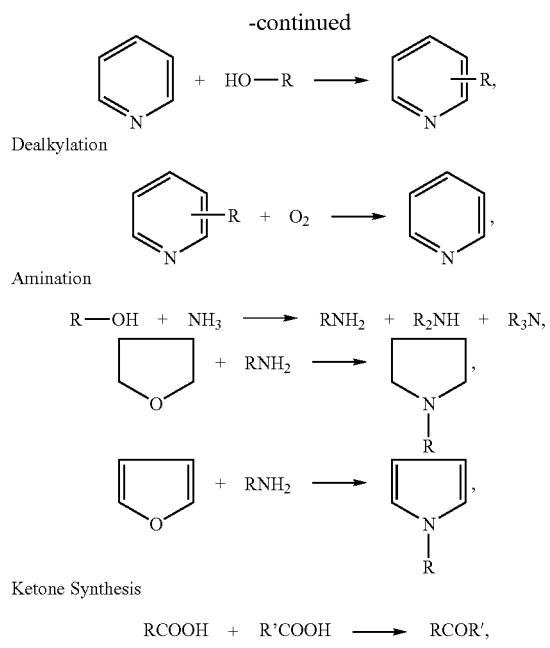

Dealkylation

Amination

Ketone Synthesis wherein R represent any chemical functional group which does not alter the chemical compounds.

Other reactions in which the activated carbon monolith catalyst may participate includes, but are not limited to, chlorination, isomerization, heterobicyclic compounds synthesis, polymerization, hydrodesulfurization, and hydrodenitrogenation.

It is appreciated that one of ordinary skilled in the art, presented with the teaching of the present invention, may arrive at all the available permeations of reactants and catalytic reaction reactions.

The present invention is described above and further illustrated below by way examples which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the scope of the invention and the appended claims.

Example 1

Approximately 2 L of de-ionized water was added to a 3 L heated glass reactor, and agitated by a variable speed motor attached to a plastic impeller. The temperature was ambient, and recorded via a thermocouple connected to a recording device. A quantity of sodium carbonate was added to the water in the stirring reactor so as to elevate the pH to about 10.5.

A finished self-supporting activated carbon monolith made in accordance with U.S. Pat. No. 5,914,294 was placed in the reactor so as to have the sodium carbonate aqueous solution pass evenly through the cells of the monolith as the solution was agitated.

In another glass container, a solution of palladium chloride was prepared so as to have a palladium metal loading by weight of the carbon monolith of 0.1%. The pH of this solution was adjusted to a pH of 4.0 using sodium bicarbonate. This solution was metered into the reactor.

After the metering of the palladium solution, the reactor was heated via an electronic temperature controlled device, so as to ramp to 65° C. in 30 minutes.

After the temperature of the reactor had stabilized at 65° C., a solution of sodium formate in water was metered into the reactor, and the reactor was allowed to stir for an additional 30 minutes.

Power to the heater was turned off and the reactor was allowed to cool to below 40° C., after which agitation was stopped, and the activated carbon monolith catalyst removed and washed free of any minerals, such as chlorides, by the use of de-ionized water.

Example 2

In the same manner of Example 1, a finished self-supporting activated carbon monolith made in accordance with U.S. Pat. No. 5,914,294 was used to prepare a catalyst with a palladium metal loading of 5% by weight of the activated carbon monolith catalyst.

Ingredients were increased proportionally to the amount of palladium metal used in this Example 2, as compared to Example 1.

Example 3

The activated carbon monolith catalyst of Example 2 was tested for its catalytic activity using nitrobenzene as a test reactant.

The activated carbon monolith catalyst was placed in the 500 ml glass bottle of a Rocking Parr Bomb. A quantity of 2 ml of pure nitrobenzene was added to the glass bottle along with 50 ml of methanol to act as a solvent. The bottle was inserted into the Rocking Parr Bomb at ambient temperature, which was 22° C. at the time of the test.

The bottle was pressurized to 60 psig with pure hydrogen. When agitation of the bottle commenced, time and hydrogen pressure in the bottle were recorded. Hydrogen pressure was seen to fall from 60 psig to 43.5 psig in 255 seconds. The temperature of the contents of the bottle were seen to rise from 22° C. to 31° C. in the same time period. These are direct indications of a catalytic reaction occurring with the nitrobenzene and hydrogen due to the presence of the activated carbon monolith catalyst in the bottle.

Further assurances of the reaction were test runs with no activated carbon monolith catalyst present in the test bottle containing the nitrobenzene and methanol solution as described above, where no temperature increase or drop in hydrogen pressure from 60 psig was observed, and another run with palladium sponge replacing the carbon monolith catalyst, where a very slight drop in hydrogen pressure was observed, but no appreciable temperature change was observed.

While the invention has been described in detail with respect to specific embodiments thereof it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereof.

The invention claimed is:

1. A method for catalytic hydrogenation reaction comprising contacting at least one reactant with an activated carbon monolith catalyst under hydrogen pressure, the activated carbon monolith catalyst comprising (a) a porous finished activated carbon monolith having walls defining at least one passage therethrough and comprising a supporting ceramic matrix and substantially discontinuous activated carbon particles dispersed throughout the supporting ceramic matrix, the walls having an exterior surface, depth, and passageways into the depth of the walls, and (b) at least one catalyst precursor on said porous finished-activated carbon monolith, the at least one catalyst precursor applied to the porous finished activated carbon monolith and disposed on the exterior surface of the walls and within the passageways into the depth of the monolith walls of the porous finished activated carbon monolith, wherein the at least one catalyst precursor is catalytically active.

2. A method as in claim 1, wherein the at least one catalyst precursor is selected from the group consisting of reduced precious metal, precious metal oxide, precious metal with modifier, base metal, and a combination thereof, wherein the base metal is selected from the group consisting of zinc, nickel, copper, manganese, iron, chromium, vanadium, and molybdenum.

3. A method as in claim 1, wherein the at least one catalyst precursor includes a modifier selected from the group consisting of potassium hydrated oxides, potassium hydroxides, calcium hydrated oxides, calcium hydroxides, magnesium hydrated oxides, magnesium hydroxides, sodium hydrated oxides, and sodium hydroxides.

4. A method as in claim 1, wherein the at least one catalyst precursor is a precious metal selected from the group consisting of palladium, platinum, rhodium, ruthenium, iridium, osmium, silver, and gold.

5. A method as in claim 1, wherein the at least one catalyst precursor is a base metal selected from the group consisting of zinc, nickel, copper, manganese, iron, chromium, vanadium, and molybdenum.

6. A method as in claim 1, wherein the at least one catalyst precursor is a base metal catalyst selected from the group consisting of oxides, hydrated oxides, and carbonates.

7. A method as in claim 1, wherein the at least one catalyst precursor is present on the finished activated carbon monolith in an amount from about 0.01% to about 5.0% by weight of the activated carbon monolith catalyst.

8. A method as in claim 1, wherein the finished activated carbon monolith has an axial crushing strength from about 500 to about 1600 psi.

9. A method as in claim 1, wherein the activated carbon particles are present in the finished activated carbon monolith in an amount from about 20 to about 95% by weight of the monolith and the supporting matrix is present in the finished activated carbon monolith in an amount from about 80 to about 5% by weight of the finished activated carbon monolith.

10. A method as in claim 1, wherein the activated carbon particles are characterized by a nitrogen B.E.T. surface area from about 600 to about 2000 $m^2/g$.

11. A method as in claim 1, wherein the activated carbon particles are characterized by having a particle size such that more than 40% by weight of the activated carbon passes through a 200 mesh screen.

12. A method as in claim 1, wherein the finished activated carbon monolith is made according to a process comprising extruding an extrudable mixture comprising the activated carbon particles, a ceramic forming material, a flux material and water, drying the extruded monolith, and firing the dried monolith at a temperature and for a time period sufficient to fuse the ceramic forming material together and form the ceramic matrix.

13. A method as in claim 12, wherein the flux material is a feldspathic mineral.

14. A method as in claim 13, wherein the feldspathic mineral is nepheline syenite.

15. A method as in claim 12, wherein the flux material further comprises sodium silicate.

16. A method as in claim 12, wherein the ceramic forming material is selected from the group consisting of ball clay, plastic kaolins, smectite clay minerals, bentonite, and combinations thereof.

17. A method as in claim 12, wherein the ceramic forming material further comprises a shrinkage reducing filler material.

18. A method as in claim 1, wherein the finished activated carbon monolith further has a plurality of passages therethrough for receiving a flow of fluid and an open frontal area greater than 50% and up to 85%.

19. A method as in claim 1, wherein the finished activated carbon monolith is honeycomb shaped.

20. A method as in claim 1, wherein the activated carbon particles have pores and the at least one catalyst precursor is at least partially disposed in pores of the activated carbon.

21. A method as in claim 1, wherein the at least one reactant is a neat organic liquid.

22. A method as in claim 1, wherein the at least one reactant is dissolved in an organic solvent.

* * * * *